(12) United States Patent
Akahane et al.

(10) Patent No.: US 6,410,560 B1
(45) Date of Patent: Jun. 25, 2002

(54) DRUG FOR RELIEVING PAIN AND PROMOTING THE REMOVAL OF CALCULI IN UROLITHIASIS

(75) Inventors: Masuo Akahane; Yoshitaka Tomiyama, both of Nagano (JP)

(73) Assignee: Kissei Pharmaceutical Co., Ltd. (JP)

( * ) Notice: Subject to any disclaimer, the term of this patent is extended or adjusted under 35 U.S.C. 154(b) by 0 days.

(21) Appl. No.: 09/448,423

(22) Filed: Nov. 24, 1999

Related U.S. Application Data

(60) Division of application No. 09/077,293, filed on May 29, 1998, now abandoned, which is a continuation-in-part of application No. PCT/JP96/03494, filed on Nov. 29, 1996, now abandoned.

(30) Foreign Application Priority Data

Nov. 30, 1995 (JP) ................................................ 7-346599

(51) Int. Cl.$^7$ .......................... A61K 31/47; A61K 31/36; A61K 31/24; A61K 31/195
(52) U.S. Cl. ........................ 514/312; 514/465; 514/539; 514/567
(58) Field of Search ................................. 514/629, 653, 514/312, 465, 539, 567

(56) References Cited

PUBLICATIONS

Galitzky et al, American Journal of Physiology, vol. 264, No. 3, Part 1, pp. E403–E412, 1993.*
Medline abstract, AN 96165630, Morita, T. et al (Aug. 1995).
HCAPLUS abstract, AN 1989:400644, Morita T. (1989).
Melchior, H., Spasmolysis through Beta–adrenergic Drugs, vol 10, No. 4, pp. 183–188 (1971).
Morita, T., Urol. Int., vol. 45, No. 1, pp. 10–15 (1990).
Longrigg, J.N., J.R. Coll. Surg. Edinburg, vol. 22, No. 5, pp. 309–318, XP–002085648 (Sep. 1977).
Lindsey et al, Urol. Res., vol. 7, No. 1, pp. 13–17 (1979).
Blooch et al, Urol. Int. vol. 39, No. 5, pp. 308–311 (1984), XP–002085650.

* cited by examiner

*Primary Examiner*—William R. A. Jarvis
(74) *Attorney, Agent, or Firm*—Stuart D. Frenkel

(57) ABSTRACT

The present invention relates to a novel drug composition for relieving pain and promoting the removal of calculi in urolithiasis which contains an active ingredient having stimulating effects on both $\beta_2$- and $\beta_3$-adrenoceptors and exerting a potent relaxing effect on human ureteral smooth muscle.

6 Claims, 1 Drawing Sheet

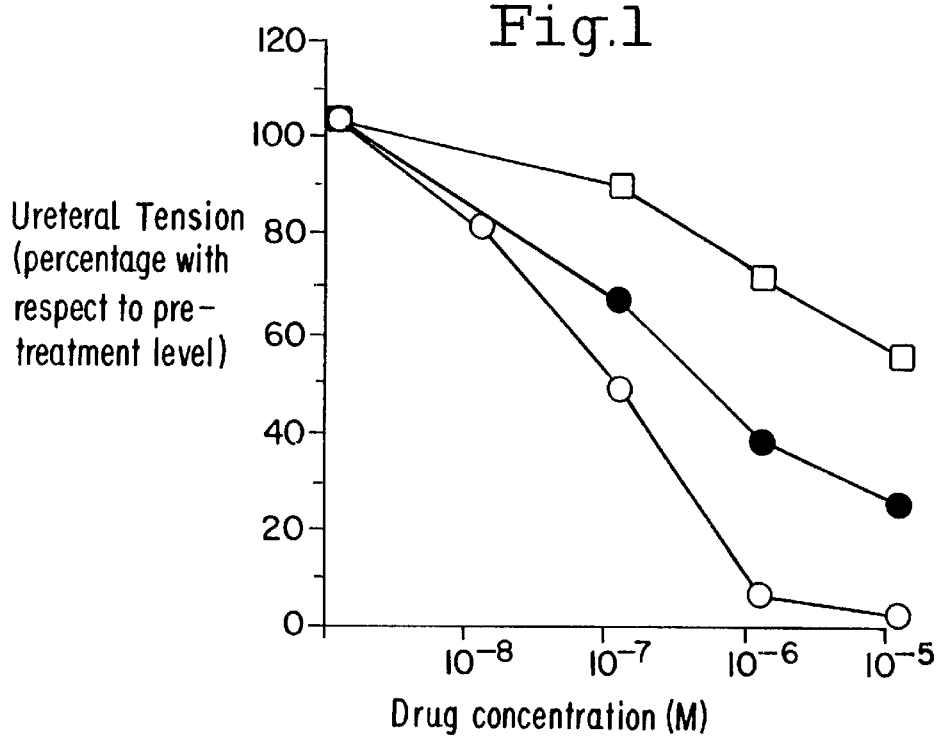
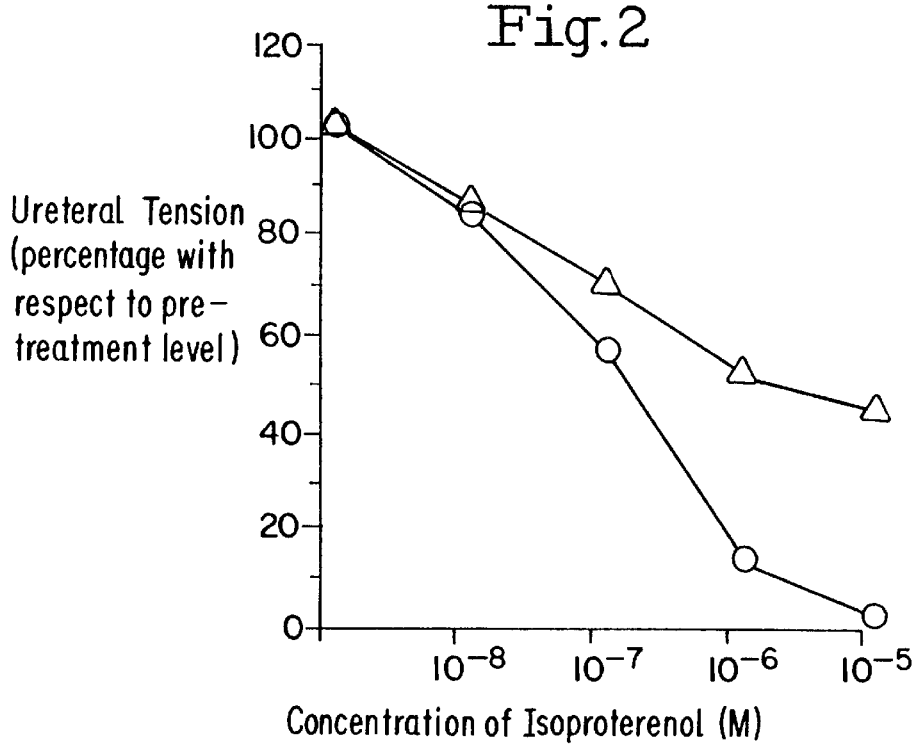

DRUG FOR RELIEVING PAIN AND PROMOTING THE REMOVAL OF CALCULI IN UROLITHIASIS

This application is a divisional of U.S. application Ser. No. 09/077,293, filed May 29, 1998, now abandoned which is a Continuation-in-part of International Application PCT/JP96/03494, International filing date Nov. 29, 1996, which designated the United States and is now abandoned.

TECHNICAL FIELD

The present invention relates to drug compositions for relieving pain and promoting the removal of calculi in urolithiasis. The drug compositions of this invention contain active ingredients having stimulating effects on both $\beta_2$- and $\beta_3$-adrenoceptors.

BACKGROUND OF THE INVENTION

It is known that three subtypes of $\beta$-adrenoceptor, which have been classified as $\beta_1$, $\beta_2$ and $\beta_3$ are present in the human body. Each receptor subtype is distributed in specified organs. $\beta_1$-Adrenoceptor is mainly present in the heart and its stimulation enhances the function of the heart. $\beta_2$-Adrenoceptor is mainly present in the trachea, peripheral blood vessels and the uterus. Smooth muscle of such organs is relaxed by the stimulation of this receptor. In addition, it has recently been reported that $\beta_3$-adrenoceptor is present in the digestive tract and adipocytes. The stimulation of $\beta_3$-adrenoceptor leads to the relaxation of gastrointestinal smooth muscle, lipolysis and energy expenditure in adipose tissues and so on.

Thus, the distribution of $\beta$-adrenoceptor subtypes is specified by organs and tissues. Various receptor subtypes including $\beta$-adrenoceptor have been actively studied for developing more effective medicinal treatment of some diseases. Consequently, efforts have been paid extensively to develop more effective and highly selective drugs that act upon a specified organ. However, $\beta$-adrenoceptor subtypes distributed in human ureter have not yet been elucidated, although the progress of studies to develop drugs that act more effectively on human ureter has been desired.

Urolithiasis is a disease generating calculi in the lumen of the entire urinary tract from kidney to urethra. The calculi is thought to be formed in a series of events such as nucleation of urinary component, crystallization, aggregation, concretion and enlargement. Urinary flow is often obstructed by calculi, which results in the rise of intra-ureteral pressure leading to pain. An analgesic and an antispastic are prescribed for the pain. However, the use of the analgesic is only temporary symptomatic therapy for the pain, and is not expected to fundamentally treat urolithiasis. The effectiveness of an anti-cholinergic, one of the antispastics, is also not satisfactory. Therefore, drugs which can relieve pain and promote the removal of calculi by widening the ureter due to strong relaxing effects are desired (The Journal of Urology, Vol. 152, pp. 1095–1098 (1994)).

SUMMARY OF THE INVENTION

The present inventors have extensively studied drug effects on the human ureter in order to elucidate the $\beta$-adrenoceptor subtypes distributed therein. As a result, it has been surprisingly found that $\beta_3$-adrenoceptor in addition to $\beta_2$-adrenoceptor was present in human ureter, thereby forming the basis of the present invention.

Accordingly, the present invention is to provide novel drugs for relieving pain and for promoting the removal of calculi in urolithiasis. Useful drugs of this invention contain active ingredients which exert a strong relaxing effect on human ureteral smooth muscle by stimulating both $\beta_2$- and $\beta_3$-adrenoceptors.

BRIEF DESCRIPTION OF THE DRAWINGS

FIG. 1 illustrates the effect of each drug on contraction of isolated human ureteral smooth muscle induced by 40 mM of potassium chloride. The ordinate axis shows the change of ureteral tension after treatment of each drug. The ureteral tension before the treatment is indicated as 100%, and the tension after the treatment of $10^{-5}$ M of isoproterenol which produces maximal relaxation of ureter is indicated as 0%. The abscissa shows drug concentrations (M). The marks -o-, -●- and -□- represent compounds isoproterenol, procaterol and CGP12,177A, respectively.

FIG. 2 illustrates the effect of each drug on contraction of isolated human ureteral smooth muscle induced by 40 mM of potassium chloride. The ordinate axis shows the change of ureteral tension after treatment of each drug. The ureteral tension before the treatment is indicated as 100%, and the tension after the treatment of $10^{-5}$ M of isoproterenol alone which produces maximal relaxation of ureter is indicated as 0%. The abscissa shows concentrations (M) of isoproterenol. The marks -o- and -Δ- represent isoproterenol alone and isoproterenol in the presence of 100 nM of ICI-118,551, respectively.

DETAILED DESCRIPTION OF THE INVENTION AND BEST MODE

The present inventors conducted experiments using isoproterenol as a nonselective $\beta$-adrenoceptor stimulant, procaterol as a selective $\beta_2$-adrenoceptor stimulant, CGP-12,177A hydrochloride [chemical name: (±)-4-[3-[(1,1-dimethylethyl)amino]-2-hydroxypropoxy]-1,3-dihydro-2H-benzimidazol-2-one hydrochloride] as a selective $\beta_3$-adrenoceptor stimulant having $\beta_1$- and $\beta_2$-adrenoceptor blocking activity (Molecular Pharmacology, Vol. 44, pp. 1094–1104 (1993)), and ICI-118,551 hydrochloride [chemical name: (±)-1-[(2,3-dihydro-7-methyl-1H-inden-4-yl)oxy]-3-[(1-methylethyl)amino]-2-butanol hydrochloride] as a selective $\beta_2$-adrenoceptor blocker.

Investigated were the effects of the drugs on contraction of human ureteral smooth muscle induced by potassium chloride. What was found was that both procaterol, a selective $\beta_2$-adrenoceptor stimulant, and CGP-12,177A, a selective $\beta_3$-adrenoceptor stimulant, produced apparent relaxation of the smooth muscle. This result affirmed that $\beta_3$-adrenoceptor is present in human ureter in addition to $\beta_2$-adrenoceptor.

Furthermore, the effects of isoproterenol alone and isoproterenol combined with ICI-118,551 were compared in similar experiments using human ureteral smooth muscle. It was found that the relaxing effect of isoproterenol on ureteral smooth muscle is not blocked completely by ICI-118,551, a selective $\beta_2$-adrenoceptor blocker. Therefore, it was confirmed pharmacologically that $\beta_3$-adrenoceptor in addition to $\beta_2$-adrenoceptor are present in human ureter.

Thus, it is clear that both $\beta_2$- and $\beta_3$-adrenoceptors are present in human ureter. Accordingly, drugs having stimulating effects on both $\beta_2$- and $\beta_3$-adrenoceptors can provide clinically satisfactory relaxation of human ureter, which can not be attained by using the existing drugs. Drugs having stimulating effects on both $\beta_2$- and $\beta_3$-adrenoceptors are very useful for relieving pain and promoting the removal of calculi in urolithiasis.

Drugs having stimulating effects on both $\beta_2$- and $\beta_3$-adrenoceptors of the present invention have excellent relaxing effects on human ureteral smooth muscle, and are useful for relieving pain, promoting spontaneous passage of calculi and the removal of calculi after extracorporeal shock wave lithotripsy and so on.

Useful compositions of this invention will include active ingredients having stimulating effects on both $\beta_2$- and $\beta_3$-adrenoceptors, simultaneously, and which can be effective in a range of usual dose.

The drug compositions of this invention can include as active ingredients, a single compound having simultaneous stimulating effects on both $\beta_2$- and $\beta_3$-adrenoceptors or, a mixture of compounds which collectively stimulate both of the $\beta_2$- and $\beta_3$-adrenoceptors. Single compounds having selective stimulating effects on both $\beta_2$- and $\beta_3$-adrenoceptors are preferable. For example, formoterol (chemical name: 2-hydroxy-5-[(1RS)-1-hydroxy-2-[[(1RS)-2-(p-methoxyphenyl)-1-methylethyl]amino]ethyl]-formanilide) can be illustrated. $EC_{50}$ ratios of $\beta_2$-adrenoceptor stimulating effect to $\beta_3$-adrenoceptor stimulating effect having values ranging from about 1/100 to 100/1 are preferable, while ratio values ranging from about 1/10 to 10/1 are more preferable. Additional compounds which can be used for selectively stimulating $\beta_3$-adrenoceptor include BRL-37344, CL-316243 and SR-58611A.

Usually, $EC_{50}$ values for $\beta_2$-adrenoceptor stimulating effects can be calculated by measuring inhibitory effects on spontaneous uterine contractions of pregnant rats. For example, the $EC_{50}$ value for formoterol was $4.2 \times 10^{-10}$(M).

Usually, $EC_{50}$ values for $\beta_3$-adrenoceptor stimulating effects can be calculated by measuring inhibitory effects on spontaneous contractions of ferret ureteral smooth muscle. For example, the $EC_{50}$ value for formoterol was $5.1 \times 10^{-8}$(M).

The drugs having markedly weakened $\beta_1$-adrenoceptor stimulating effects are preferred to reduce burdens on heart and not to induce side effects such as tachycardia.

EXAMPLE

The present invention is further illustrated in more detail by way of the following Examples. The present invention is not limited thereto.

Measurement of the contractile force of the ureteral smooth muscle strip (1) Preparation of smooth muscle strips Specimens of human ureter were obtained from patients undergoing nephrectomy or total cystectomy. After the specimens were carefully dissected free from the surrounding fat tissues, they were cut into spiral strips. The ureteral strips of about 20 mm in length and 5 mm in width were prepared.

(2) Experimental conditions

Buffer solution; Locke's-solution No.2: NaCl (154 mM), KCl (5.6 mM), CaCl$_2$ (2.1 mM), NaHCO$_3$ (5.6 mM) and glucose (3.6 mM)

Ureteral muscle strips without any spontaneous rhythmic contractions were used. An initial resting tension of about 1.0 g was placed. The actions of drugs against the 40 mM KCl-induced tonic contraction were evaluated in the presence of $10^{-6}$ M phentolamine.

The condition for measurement; The bathing solution was maintained at 37° C. and gassed with a mixture of 95% O$_2$ and 5% CO$_2$.

Drug treatment; The drug solution was added cumulatively to the organ bath every 5 minutes.

The evaluation of drugs; The drug-induced relaxation was expressed as a percentage of the maximal relaxing response to $10^{-5}$ M of isoproterenol. The ureteral tension before the treatment is indicated as 100%, and the tension after treatment of $10^{-5}$ M of isoproterenol which produces maximal ureteral relaxation is indicated as 0%.

EXAMPLE 1

According to the methods described above, the ureteral relaxing effects of the drug were measured using the human ureteral smooth muscle strips.

Drugs: 1. isoproterenol, 2. procaterol and 3. CGP-12,177A hydrochloride

The results are as follows (FIG. 1): CGP-12,177A, a selective $\beta_3$-adrenoceptor stimulant, as well as procaterol, a selective $\beta_2$-adrenoceptor stimulant, produced apparent ureteral relaxation. Moreover, isoproterenol, a non-selective $\beta$-adrenoceptor stimulant, which stimulates both $\beta_2$- and $\beta_3$-adrenoceptors, also showed a more potent relaxing effect. These results demonstrate that the relaxation of human ureteral smooth muscle is mediated via $\beta_3$-adrenoceptors in addition to $\beta_2$-adrenoceptors.

EXAMPLE 2

According to the method described above, the interaction between a $\beta$-adrenoceptor stimulant and a $\beta$-adrenoceptor blocker was evaluated in human ureteral smooth muscle strips using the following drugs.

Drugs: 1. isoproterenol and 2. ICI-118,551 hydrochloride

The results are as follows (FIG. 2): The pre-treatment with ICI-118,551 (100 nM), a selective $\beta_2$-adrenoceptor blocker, attenuated the isoproterenol-induced ureteral relaxation, but did not completely block. Isoproterenol still produced a relaxation by about 50%, even if 100 nM of ICI-118,551 was present. Judging from these results, it is also demonstrated that the relaxation of human ureteral smooth muscle is mediated via $\beta_3$-adrenoceptors in addition to $\beta_2$-adrenoceptors and that considerable numbers of $\beta_3$-adrenoceptors exist in human ureteral smooth muscle.

EXAMPLE 3

The experiment for measuring the $\beta_2$-adrenoceptor stimulating effect (The effects of the drug on the spontaneous contraction in the isolated uterus of the pregnant rat)

The uterus of pregnant SD rats (pregnancy day of 21) was isolated and longitudinal smooth muscle strips ( about 15 mm in length and 5 mm in width) free from the basal plate were prepared. The experiment was conducted according to the Magnus method. The preparations were mounted with an initial resting tension of about 1.0 g in the Locke's-Ringer solution maintained at 37° C. and gassed with a mixture of 95% O$_2$ and 5% CO$_2$. The spontaneous contraction of the uterus was measured by an isometric force-transducer and recorded in a rectigraph. The drug solution was added cumulatively to the organ bath every 5 minutes. Uterine activities were calculated as the sum of the amplitudes of the spontaneous contraction for 5 minutes, and the percent change before and after the drug application were compared. The $EC_{50}$ value was determined as the molar concentration required to produce 50% of own maximal relaxation elicited by each drug.

EXAMPLE 4

The experiment for measuring the $\beta_3$-adrenoceptor stimulating effects (The effects of the drug On the spontaneous rhythmic contraction in the isolated ferret ureter)

The ferret ureter was isolated and the ring smooth muscle strips were prepared (about 20 mm in length). The experiment was conducted according to the Magnus method. The preparations were mounted with an initial resting tension of about 0.5 g in the Krebs-Henseleit solution maintained at 37° C. and gassed with a mixture of 95% $O_2$ and 5% $CO_2$. The spontaneous contraction of the ureter was measured by an isometric force-transducer and recorded in a rectigraph. The drug solution was added cumulatively to the organ bath every 5 minutes. Ureteral activities were calculated as the sum of the amplitudes of the spontaneous contraction for 5 minutes, and the percent change before and after the drug application were compared. The $EC_{50}$ value was determined as the molar concentration required to produce 50% of own maximal relaxation elicited by each drug.

Industrial Applicability

A drug composition which contains as active ingredients one or more drug compounds which collectively have stimulating effects on both $\beta_2$- and $\beta_3$-adrenoceptors and which exert a potent relaxing effect on human ureteral smooth muscle. The drug compositions of this invention are capable of relieving pain and for promoting the removal of calculi in urolithiasis.

What is claimed is:

1. A drug composition for relieving pain and promoting the removal of calculi in urolithiasis, containing active ingredients in the form of a mixture of different compounds, each of which compounds has selective stimulating effects on one or both $\beta_2$- and $\beta_3$-adrenoceptors, and which mixture collectively has selective stimulating effects on both $\beta_2$- and $\beta_3$-adrenoceptors.

2. The drug composition of claim 1, wherein said mixture comprises a first compound having selective stimulating effects on both $\beta_2$- and $\beta_3$-adrenoceptors, and a second compound having selective stimulating effects on either the $\beta_2$-adrenoceptor or $\beta_3$-adrenoceptor.

3. The drug composition of claim 1 wherein said mixture comprises a first compound having selective stimulating effects on $\beta_2$-adrenoceptors and a second compound having selective stimulating effects on $\beta_3$-adrenoceptors.

4. The drug composition of claim 3 wherein said first compound is procaterol.

5. The drug composition of claim 3 wherein said second compound is selected from the group consisting of BRL-37344, CL-316243, SR-58611A and mixtures thereof.

6. The drug composition of claim 3 wherein said first compound is procaterol and said second compound is BRL-37344, CL-316243, or SR-58611A.

* * * * *